United States Patent
Liu

(10) Patent No.: US 8,158,169 B2
(45) Date of Patent: Apr. 17, 2012

(54) CHINESE MEDICINE COMPOSITION AND PREPARATION METHOD AND USE THEREOF

(76) Inventor: Jianxun Liu, Beijing (CN)

(*) Notice: Subject to any disclaimer, the term of this patent is extended or adjusted under 35 U.S.C. 154(b) by 596 days.

(21) Appl. No.: 12/297,643

(22) PCT Filed: Apr. 19, 2006

(86) PCT No.: PCT/CN2006/000724
§ 371 (c)(1),
(2), (4) Date: Jan. 30, 2009

(87) PCT Pub. No.: WO2007/118363
PCT Pub. Date: Oct. 25, 2007

(65) Prior Publication Data
US 2009/0238902 A1    Sep. 24, 2009

(51) Int. Cl.
*A61K 36/16* (2006.01)
*A61K 36/48* (2006.01)
*A61K 36/00* (2006.01)

(52) U.S. Cl. .................. 424/752; 424/757; 424/725

(58) Field of Classification Search .................. None
See application file for complete search history.

(56) References Cited

FOREIGN PATENT DOCUMENTS
CN    1413656 A    4/2003

OTHER PUBLICATIONS

DW ACC 2003-569994, Apr. 2003, DW or CN 141365, Liu.*
DW ACC 2006-274181, Dec. 2005, DW or CN 170405, Zhaq.*
DW ACC 2005-659494, May 2005, DW or CN 161830, Wang.*
DW ACC 2003-587922, May 2003, DW or CN 141869, Lin et al.*
Su Li, Food and Nutrition in China, No. 9, 2004, "Soybean, perfect nutritional and health food", P42 (incuding partial English translation).
Liu et al., "Effect of combination of extracts of ginseng and ginkgo biloba on acetylcholine in amyloid beta-protein-treated rats detemined by an improved HPLC", Acta Pharmacol Sin. Sep. 25, 2004, (9): pp. 1118-1123.
Morris et al. "Place navigation impaired in rats with hippocampal lesions", Nature, vol. 297, Jun. 24, 1982, pp. 681-683.

* cited by examiner

*Primary Examiner* — Christopher R Tate
*Assistant Examiner* — Randall Winston
(74) *Attorney, Agent, or Firm* — Edwards Wildman Palmer LLP; Jeffrey D. Hsi; Mark D. Russett

(57) ABSTRACT

This invention relates a traditional Chinese medicine composition and the drug containing this composition as well as preparation method and use thereof. The composition comprises 1-10 parts by weight of radix ginseng, 1-10 parts by weight of folium ginkgo, 0.05-0.5 parts by weight of stigma croci and 5-10 parts by weight of *glycine max* l. merrill. The components can be the traditional Chinese medicinal materials or the extracts obtained by extracting the same quantity of the Chinese medicinal material. The Chinese medicine composition can be used for the treatment of ischemic cerebrovascular disease and senile dementia.

14 Claims, No Drawings

CHINESE MEDICINE COMPOSITION AND PREPARATION METHOD AND USE THEREOF

RELATED APPLICATION

This application is the 35 U.S.C. §371 national stage of PCT application no. PCT/CN2006/000724, filed Apr. 19, 2006.

TECHNICAL FIELD OF INVENTION

This invention relates to a traditional Chinese medicine composition, more specifically, a traditional Chinese medicine composition used for the treatment of ischemic cerebrovascular disease and senile dementia. The components constituting the composition could be the traditional Chinese medicinal materials that are directly crushed into powder, and/or the extracts obtained through extraction of Chinese medicinal materials.

BACKGROUND OF TECHNOLOGY

Cerebrovascular disease is usually divided into two types, ischemic cerebrovascular disease and hemorrhagic cerebrovascular disease, with the ischemic cerebrovascular disease being more common and the cerebral infarction accounting for 59.2%-85%. Ischemic cerebrovascular disease comprises 1) the transient ischemic attack (TIA, also known as mini stroke or transitory ischemic attack), which is a dysfunction caused by a transient, ischemic and focal injury to the brain tissue, and is related to cerebral arteriosclerosis in its etiology; 2) cerebral thrombosis, which results from blood clotting in the case of the atherosclerosis, a variety of arteritises, trauma or other physical factors, or local cerebrovascular lesions due to blood diseases; 3) cerebral embolism, caused by embolisms generated from multiple diseases entering the blood and blocking the cerebral vessels.

Many drugs are now available for the treatment of ischemic cerebrovascular disease. The allopathic medicines are primarily the thrombolytic, antiplatelet and anticoagulant drugs, while the traditional Chinese drugs mainly comprise the Huoxue Huayu (promoting blood circulation and removing blood stasis) traditional Chinese drug injections represented by radix salivae miltiorrhizae and panax notogiseng saponins, the Qingre Jiedu, Xingnao Kaiqiao (clearing away heat and toxic substances) traditional Chinese drug injections represented by Xing Nao Jing and Qing Kai Ling and the Yiqi Huoxue Tongluo (supplementing Qi, promoting blood circulation, removing obstruction in collaterals) oral preparations represented by Ren Shen Zai Zao Wan (radix ginseng reconstruction pills) and Hua Tuo Zai Zao Wan (Hua Tuo reconstruction pills). In clinical practice, the allopathic drugs are mainly used in emergency situation and have evident adverse effects while the traditional Chinese medicine injections are not available for long-term use and the Chinese medicine compound have many problems such as uncertain effect, unclear effective components and lack of stable quality control standard.

Dementia is an acquired consistent mentality impairment syndrome induced by organic pathological changes of the cerebrum. A global epidemiological investigation in 2005 showed that there are about 24,000,000 patients with dementia. The annual increment is 4,600,000 patients with one more patient for every 7 seconds and the number is double for every 20 years. In China, as estimated conservatively, the number will increase by 300% annually from 2001 to 2040. It is anticipated that there will be 81,000,000 patients suffering form dementia by 2040. The occurrence rate of dementia increases with the age. The senile dementia is mainly classified into: A. primary degenerative dementia, i.e. Alzheimer's disease (AD); B. vascular dementia (VD); C. mixed dementia (AD combined with VD); D. other types of dementia (Pick's disease and Dementia with Lewy bodies). AD and VD are the two most primary types in senile dementia and account for more than 90% in all dementia patients, with AD being the most common that patients over 65 years old have dementia and the most lethal.

In clinical practice, the drug of first choice for treatment of senile dementia available now is the cholinesterase inhibitors (such as tacrine, donepezil, rivastigmine, galantamine and the like). The diagnosis for the senile dementia in the traditional Chinese medicine comprises all types of AD, VD or the mixed type in allopathic medicine, including all diseases and symptoms related to senile dementia. The traditional Chinese medicine compounds commonly used for treatment of senile dementia comprise Ding Zhi Xiao Wan (radix ginseng, pachyma cocos, acorus calamus and polygala teuofolia), Tiao Xin Fang (prescription for regulating mental activities) (codonopsis pilosula, pachyma cocos, licorice, acorus gramineus soland, polygala teuofolia, etc.), Bu Shen Fang (prescription for tonifying kidney) (asparagus cochinchinesis, ophiopogon japonicus, crude radix rehmanniae, processed radix rehmanniae, fructus corni, etc.), Dang Gui Shao Yao San (radix angelicae sinensis and paeonia lactiflora powder), Huang Lian Jie Du Tang (coptis chinensis toxic materials removing liquid), Gou Teng San (ramulus uncariae cum uncis powder), Yi Gan San, Xiao Chaihu Tang (small radix bupleuri liquid) and Chai Hu Jia Long Gu Mu Li Tang (radix bupleuri, fossilized dragon's bone and oyster liquid). However, in clinical practice, the cholinesterase inhibitors can only improve the cognition disorder and the emotional symptoms, have no significant effects on fundamental pathological changes. They can only delay (for 1 to 2 years) and can not prevent the progress of the disease, i.e. they can only alleviate the symptoms but can not cure the disease. The long-term use may even induce the increase of the synthesis of the cholinesterase. Tacrine is more likely to result in the severe gastrointestinal reaction and liver toxicity. The traditional Chinese medicine compounds have many problems such as unclear effective components, inconvenience for long-term drug use and lack of stable quality control standard.

Therefore, there are obvious limitation and shortcomings in the allopathic drugs and the traditional Chinese medicines are available now for treatment of ischemic cerebrovascular disease and senile dementia, and a demand remains for the development of a type of drug for treatment of ischemic cerebrovascular disease and senile dementia with affirmative and significant effect, the perfect preparation technique and stable drug quality.

SUMMARY OF INVENTION

This invention originates from the theory of traditional Chinese medicine and is achieved by summarizing the experiences and clinical practice. This invention relates to a traditional Chinese medicine composition, which is a preparation of pure traditional Chinese medicines produced by extracting and refining from four natural plants. It is proved by experiments that this invention has an affirmative therapeutic effect and it is safe.

This invention aims at providing a traditional Chinese medicine composition as well as the drugs comprising said composition. This drug can be used for treatment of ischemic cerebrovascular disease and senile dementia.

This invention also aims at providing a preparation method of the said composition, by which the Chinese medicine composition with significant therapeutic effect and stable quality that can be used for treatment of ischemic cerebrovascular disease and senile dementia can be obtained.

This invention also aims at providing the use of the said Chinese medicine composition in preparing the drugs for treatment of ischemic cerebrovascular disease and senile dementia.

To achieve the said aim, this invention provides a traditional Chinese medicine composition, comprising 1-10 parts by weight of radix ginseng, 1-10 parts by weight of folium ginkgo, 0.05-0.5 parts by weight of stigma croci and 5-10 parts by weight of *glycine max* l. merrill. Each of the said radix ginseng, folium ginkgo, stigma croci and *glycine max* l. merrill (ripe seed of *Glycine max* (L.) Merr.) can be obtained from the raw material or extracted from the same quantity of the traditional Chinese medicinal material.

The said Chinese medicine composition in this invention is developed for the systemic treatment of ischemic cerebrovascular disease and senile dementia. It is a compound of traditional Chinese medicines and emphasizes the improvement of the autoimmune system. The said Chinese medicinal materials can be easily obtained in bulk. They have no toxic or adverse effects with rational combination and good effect.

The weight ratio of the components in the traditional Chinese medicine composition is preferably as follows: 2-6 parts by weight of radix ginseng, 3-6 parts by weight of folium ginkgo, 0.06-0.2 parts by weight of stigma croci and 7-8 parts by weight of *glycine max* l. merrill and the more preferable weight ratio is as follows: 4.0 parts by weight of radix ginseng, 4.5 parts by weight of folium ginkgo, 0.1 parts by weight of stigma croci and 7.5 parts by weight of *glycine max* l. merrill.

The yield of extraction for the traditional Chinese medicines in the said composition is different from each other. Thus, this invention also provides a Chinese medicine composition comprising 1-10 parts by weight of the extract of radix ginseng, 1-10 parts by weight of the extract of folium ginkgo, 0.5-5 parts by weight of the extract of the stigma croci and 0.1-1 parts by weight of the extract of the *glycine max* l. merrill. All the said extracts of radix ginseng, folium ginkgo, stigma croci and *glycine max* l. merrill are alcohol extracts.

The design of the prescription of the Chinese medicine composition in this invention is rational. Radix ginseng in the composition is the monarch drug (main drug) according to the principle of traditional Chinese medicine. AD to be treated with the composition of this invention is characterized by deficiency in origin and excess in superficiality, and is mainly related to deficiency of the viscera and disorder of Qi and Blood. The deficiency of the viscera and turbid toxin blocking the brain collaterals are the fundamental pathological causes and maintain for the whole course of the disease. The monarch drug radix ginseng in the prescription (the effective components is ginsenosides) can greatly nourish renal Qi and tranquilize mentality for increase of intelligence. The ministerial drug (subordinate drug) folium ginkgo (the main effective components are flavonoids of *ginkgo* and ginkgolides) and stigma croci (the main effective components are stigma croci glycosides) can promote the blood circulation and remove the toxic substances. The adjuvant drug *glycine max* l. merrill (the main effective components are *glycine max* l. merrill isoflavonoids and Vitamin E) can remove the endogenous toxins. The composition can supplement Qi and promote blood circulation, remove toxic substances and dredge collaterals, and tranquilize mentality to increase intelligence with both the origin and the superficiality considered.

The composition of this invention can be produced by adding and mixing either the raw powders of the said Chinese medicinal materials or the extracts of the said Chinese medicinal materials. The composition can be effective in the treatment of ischemic cerebrovascular disease and senile dementia, provided that the compositions with the said weight ratios are included, which can be within the protection scope of this invention. The radix ginseng, folium ginkgo, stigma croci and *glycine max* l. merrill are all ethanol extracts of the Chinese medicinal materials in the preferable embodiments of this invention.

In the preferable embodiments, the components and the weight ratio of the said composition are as follows: the extract of radix ginseng: the extract of folium ginkgo: the extract of stigma croci: the extract of *glycine max* l. merrill=5:5:1:0.5.

The said extract of radix ginseng can be prepared with any public known methods.

The preferable extraction method in this invention is as follows:

The low concentration (50-70%, preferably 60%) ethanol of at least 2-fold (preferably 8-fold) of quantity of radix ginseng are added into radix ginseng and at least once (preferably 3 times) of extraction is performed, at least one hour (preferably 3 hours) once. The liquid extracts are combined and concentrated till the relative density is around 1.05 (50° C.). The liquid concentrate is added with distilled water of at least one-fold (preferable 2-fold) volume and filtered. The filtrate is chromatographed on the low-polar polystyrene type macroporous adsorptive resin (preferably AB-8 Type). The resin with drugs is eluted by distilled water, followed by 10% ethanol. The 10% ethanol and water eluent is discarded and the resin is eluted with the 70% ethanol till the volume is about 2.5-fold of the volume of the column. The 70% ethanol eluent is collected and the extract of radix ginseng containing the ginsenosides can be obtained.

In this invention, the macroporous resin with drug is eluted with water, 10% ethanol and 70% ethanol respectively. The screening of the said two concentrations of the ethanol and the procedure of elution can guarantee not only the requirement of the technology for the content of the total components of the traditional Chinese medicines, but also the higher transferring rate and yield of production for the effective components.

The extract of the folium ginkgo can be obtained with the following extraction method:

The low concentration (60-80%, preferably 70%) ethanol of at least 2-fold (preferably 8-fold) of quantity of dry folium ginkgo are added into said folium ginkgo and at least one time (preferably 3 times) of extraction is performed at 50-70° C. (preferably 60° C.), at least one hour (preferably 4 hours) once. The liquid extracts are combined and concentrated by decompression till the relative density is around 1.05 (50° C.). The liquid concentrate is added with water, cooled, precipitated and filtered. The filtrate is chromatographed on the polar hydrogen bond polystyrene type macroporous adsorptive resin (preferably ADS-17 Type) for enriching the effective components. The resin with drugs is eluted by water, followed by 60% ethanol. The water eluent is discarded while the ethanol eluent is collected and concentrated till there is no smell of alcohol. Then water of 2-fold quantity of the crude drugs is added and heated to boiling. Precipitation at room temperature continues for 24 hours. After filtering, the filtrate is chromatographed on the weak polar polystyrene type macroporous adsorptive resin (preferably DM-130 Type) for removing the impurities. The resin with drugs is eluted by water, followed by 15% and 60% ethanol. The water and 15% ethanol eluents are discarded while the 60% ethanol eluent is collected. Concentration and drying can also continue and the product of the extract of the folium ginkgo can be obtained.

The extraction technology, particularly the refining technology of folium ginkgo in this invention has broken through the limitation of the organic solvent extraction technology for removal of the impurities (mainly including ginkgo phenolic acid, polysaccharide, monosaccharide and inorganic salts). Because the hazardous impurities of the ginkgo phenolic acids have extremely low water solubility and mainly exist in the more than 60% ethanol eluent while the majority of the impurities of polysaccharide and inorganic salts can be eluted with 15% ethanol, the most of the impurities can be removed with the twice refining procedure on the macroporous adsorptive resin in this invention. Moreover, the 15-60% ethanol eluents can be collected after the 60% ethanol elution, which can guarantees the content of phenolic acid is less than 5 ppm. The ratio of the main effective components in the extract of folium ginkgo obtained through the above-said screening, i.e., the ratio of the ginkgo flavonoids to the ginkgolides, are 24:25-10, preferably 24:20-10, and more preferably 24:15. The pharmacodynamic experiment proves that the effect of the extract of folium ginkgo with this ratio is significantly higher than that of the extract of folium ginkgo EGb761 in the international standard at present, with the ginkgo flavonoids to the ginkgolides of 24:6.

The said extract of stigma croci can be prepared with any public known methods. The preferable extraction method in this invention is as follows:

60-80% ethanol of at least 5-fold (preferably 20-fold) of quantity of stigma croci are added into the stigma croci material and at least once (preferably 3 times) of extraction is performed at 60-90° C. (preferably 90° C.), at least one hour (preferably 2 hours) once. The liquid extracts are combined and concentrated till there is no smell of alcohol. The liquid concentrate is added and diluted with water of more than 1-fold of quantity of raw drugs, and filtered. The filtrate is chromatographed on the weak polar polystyrene type macroporous adsorptive resin (for example, AB-8 Type). The resin with drugs is eluted by water, followed by gradually increased concentration of less than 30% ethanol (for example, 20% ethanol is used for elution followed by 30% ethanol). At last, 70% ethanol is used for elution of the resin with drugs. The water eluent and less than 30% ethanol eluents are discarded while the 70% ethanol eluent is collected and the extract of stigma croci including stigma croci glycosides can be obtained.

Because the materials are expensive, the premise for screening the preparation technology is to guarantee the high yield. Although the selected 20% and 30% ethanol for elution in this invention seems that the difference in concentration of ethanol is only 10%, the inventor in the experiments found that the loss of stigma croci glycosides is little after the elution of 20% and 30% ethanol, and if 30% or other concentrations of ethanol is directly used for elution, it will result in big loss of the stigma croci glycosides.

The ethanol extract of the *glycine max* l. merrill can be obtained with the following extraction method:

The material *glycine max* l. merrill is extracted with 85-95% ethanol and filtered. The residue is extracted with 60-80% (preferably about 70%) ethanol and filtered. The ethanol extracts are combined and concentrated till there is no smell of alcohol. The water of 1-fold weight of materials is added, sufficiently stirred and filtered. The filtrate is chromatographed on the weak polar polystyrene type macroporous adsorptive resin, for example AB-8 type macroporous adsorptive resin. Preferably, the resin with drugs is first eluted with water and the water eluent is discarded. Then 50-65% (preferably about 60%) ethanol is used for elution. The eluent is collected and part A is obtained. The main components in part A is isoflavonoids. 90-95% ethanol is used for elution. The eluent is completely collected. The anhydrous ethanol is added for esterification. The water is added again for washing and the solution is stratified. The solution is decompressed to 0.1 MPa for degasification (preferably to 0.1 Mpa with the rotary evaporator for degasification) after the lower layer (the acid water) is removed. The sodium hydroxide is added for alcoholysis. Then the water is added for washing. The alkaline water at the lower layer is removed. The organic liquid on the top layer is decompressed to 0.1 MPa for degasification and then undergoes the membrane distillation to remove the fatty acid ethyl ester. The residue undergoes the molecular distillation (preferably under the pressure of 0.133 Pa, 0.5 mm between the evaporation plate and the condensation plate). The part B is obtained and its components are the mixed tocopherol. The parts B and A are mixed and used as the extract of the *glycine max* l. merrill in this invention.

The said extraction method for the extracts of the radix ginseng, of the folium ginkgo, of the stigma croci and of the *glycine max* l. merrill is the preparation method for the main components in the capsules of the Chinese medicine composition used in Example 1.

It is determined that there are mainly the *glycine max* l. merrill isoflavonoids and the Vitamin E in the extract of *glycine max* l. merrill of this invention, with the weight ratio: 4:2-0.5, preferably about 4:1.

This invention also provides a drug for treatment of ischemic cerebrovascular disease and senile dementia including the said traditional Chinese medicine composition and the pharmaceutically acceptable auxiliary materials. The auxiliary materials vary with the type of drug preparation. For the drug, the effective components in the extract of radix ginseng (ginsenosides) are not less than 13.75 mg/0.15 g on the basis of ginsenosides Re($C_{48}H_{82}O_{18}$). The effective components in the extract of the folium ginkgo (containing ginkgolides) are not less than 2.75 mg/0.15 g on the basis of the sum of ginkgolide A ($C_{20}H_{24}O_9$), ginkgolide B ($C_{20}H_{24}O_{10}$), ginkgolide C ($C_{20}H_{24}O_{11}$) and bilobalide ($C_{15}H_{18}O_8$). The said 0.15 g means the weight of product drugs.

The said form of preparation can be any form of preparation, preferably oral medicament, including any available formulation form of oral medicament in pharmacology, preferably the granules, capsules, the tablets, the oral liquids and the syrups. In the embodiments, the granules and capsules are preferred. It proves by the experiments that the therapeutic effect of the drugs in this invention for treatment of ischemic cerebrovascular disease and senile dementia is significantly better than that of commercially available drugs. The composition of this invention decreases the dosage maximally and while maintaining high effect and low toxicity.

The inventor has performed further investigation based on this invention to obtain a Chinese medicine composition with more stable active components and higher content of the effective components. And he found that the ratio of ginkgo flavonoids to ginkgolides in the international standard extract of folium ginkgo EGb761 is 24:6, however, the pharmacodynamic experiments carried out by the inventor prove that the best ratio of *ginkgo* flavonoids to ginkgolides in the extract of folium ginkgo for treatment of ischemic cerebrovascular disease and senile dementia is 24:15. Based on the result, the general analysis and the orthogonal design are performed for the extract of the radix ginseng, the extract of the folium ginkgo, the extract of the stigma croci and the extract of the *glycine max* l. merrill by using the actual error. The experiment behavior scores of the animals are investigated with the models of the mice with D-galactose induced the brain aging and the normal mice using the Morris water maze as the means for detection of the memory level. The comprehensive analysis of the results show that the therapeutic effect of the formula of the composition consisting of the four components is better than that of any single component, and there are interactions among the extractive of the *glycine max* l. merrill, and each of the radix ginseng and folium ginkgo extract in the formula of three components (radix ginseng, folium ginkgo and stigma croci), indicating that the *glycine max* l. merrill or its extract is necessary in making up the prescription for treatment of senile dementia.

This invention also provides the preparation method for the said all types of the oral medicament of the drugs including:

A. Granules: the dextrin or other agglutinants are added into each prescribed mixed ointments, well mixed, dried at 60~80° C. and pulverized. To this the taste corrective (for example, steviosin) is added and mixed sufficiently, then granulated and dried, and the product granules are obtained.

B. Tablets: the dextrin or other agglutinants are added into the mixed ointments, mixed homogeneously, dried at 60~80° C. and pulverized. To this the appropriate amount of agglutinants (for example starch) and the disintegrating agent (for example sodium carboxymethyl starch) are added, then mixed evenly, granulated and dried. Then the appropriate amount of lubricants (for example magnesium stearate), the disintegrating agent (sodium carboxymethyl starch) are added and mixed evenly, and pressed into the tablets. The film coating may be applied when necessary. The product tablets are obtained.

C. Capsules: the dextrin or other agglutinants are added into each prescribed mixed ointments, mixed evenly, dried and pulverized. The taste corrective (for example, steviosin) and the appropriate bulking agent (for example starch) are added and mixed evenly. The granules are dried and filled into the capsules.

D. Pills: the dextrin or other agglutinants are added into each prescribed mixed ointments, mixed evenly, dried and pulverized. To this the honey or water, or beeswax or rice flour or rice paste is added. The product pills can be made per the routine method for preparation of other pills.

The inventive composition can also be made into the honeyed pill, the water-honeyed pill, the watered pill, the pasted pill, the waxed pill and the concentrated pill. The technological procedures are routine, but the technological condition may be changed according to different conditions of the Chinese medicinal materials, which is well known for those skilled in the art.

The preparation procedures for the drugs in this invention may vary in the different products. However, this is the public well-known commonsense technology of preparation and can be omitted herewith.

In the said preferable embodiment schemes, the process conditions (the best process parameter for extraction) are based on the rate of paste and the content of the effective components and is decided by the three factor-three level orthogonal experiments.

The traditional Chinese medicinal materials used for the composition of this invention are all cited in 2005 Pharmacopoeia and all indices accord with the regulations of the pharmacopoeia in identification. Three-batch samples are detected for the arsenic salts and the heavy metals under the regulation of Chinese Pharmacopoeia 2005 Volume One Appendix IXE and IXF and the results are within the range of regulation.

The drugs of this invention conform to the pharmacopoeia hygienic standard in the hygienic examination.

This invention also provides the application of the said Chinese medicine composition in preparation of the drug for treatment of ischemic cerebrovascular disease and senile dementia.

This research shows that this drug may have different function characteristics with AChEI (acetylcholinesterase inhibitor) and EGb761 (Formal name: folium ginkgo Extractive Tablets, i.e. the standard extract of folium ginkgo) clinically used now and it has better effect. This drug will be more advantageous in market. The mechanism may be that this drug takes effect on multiple targets of the pathological changes of the ischemic cerebrovascular disease and the senile dementia including the upstream process of AD, i.e., the abnormal expression of the β-amyloid precursor protein (APP) gene, which provides the experimental basis for making up the prescription of the effective components of the traditional Chinese medicinal material for treatment of ischemic cerebrovascular disease and senile dementia.

Pharmacodynamic Tests

Test drugs: the capsules of drugs used in Example 1 (Hereafter referred as the drug of this invention);

Drugs for control: Huperzine A Tablets (Formal name: Huperzine Tablets, Henan Joyline & Joysun Pharmaceutical Stock Co., Ltd.; Main components: Huperzine A $C_{15}H_{18}N_2O$); Tanakan (formal name: folium ginkgo Extractive Tablets, Beaufour Ipsen Industrie S.A.S., France); Wei Nao Kang (produced by our laboratory, containing the extracts of radix ginseng, folium ginkgo and stigma croci).

1. Behavior Experiments 1.1 Step Down Experiment 1.1.1 Influence on Model of Mice with Scopolamine Hydrobromide Induced Memory Impairment 1.1.2 The experiment is performed as per *Nervous System Drugs* Section 5 in *Methodology of Pharmaceutical Experiment* (XU Shu-yun, et al.). The number of error of the mice in the model group in 5 minutes is significantly higher than the control group ($P<0.05$). 15 days after the drug is administered, the number of error of the mice in the positive Huperzine A group and the Tanakan group is significantly lower than the model group ($P<0.05$) and the latency for the former is significantly lengthened ($P<0.001$). The number of error in the mice of the high- and intermediate-dosage groups using the inventive drug decreases significantly ($P<0.05~0.01$) and the former has longer latency ($P<0.05$). The results are showed in Table 1.

TABLE 1

Influence on Model of Mice with Scopolamine Hydrobromide Induced Memory Impairment ($\overline{X} \pm SD$)

| Group | Dosage (mg/kg) | n | Latency (s) | Number of Error |
|---|---|---|---|---|
| Control | | 10 | 279.2 ± 65.8 | 0.3 ± 0.9 |
| Model | | 13 | 192.8 ± 107.3 | 1.2 ± 1.3# |
| Huperzine A | 0.08 | 12 | 271.8 ± 54.6*** | 0.6 ± 0.9* |
| Tanakan | 30 | 12 | 233.4 ± 71.5 | 0.7 ± 0.7* |
| Drug of This Invention | 11.5 | 12 | 209.8 ± 96.3 | 0.9 ± 1.0 |
| Drug of This Invention | 23 | 12 | 226.3 ± 111.3 | 0.6 ± 0.7** |

TABLE 1-continued

Influence on Model of Mice with Scopolamine Hydrobromide Induced Memory Impairment ($\bar{X} \pm SD$)

| Group | Dosage (mg/kg) | n | Latency (s) | Number of Error |
|---|---|---|---|---|
| Drug of This Invention | 46 | 12 | 248.5 ± 88.8* | 0.5 ± 0.7** |

Note:
compared with control group: #P < 0.05;
compared with model group: *P < 0.05, P < 0.01, *P < 0.001.

1.2 Step Through Experiment

The experiment is performed as per "Nervous System Drugs Section 5" in *Methodology of Pharmaceutical Experiment* (XU Shu-yun, et al.). The number of error of the mice in the model group in 5 minutes is significantly higher than the control group (P<0.05). 15 days after the drug is administered, compared with control group, the mice in the Tanakan group have longer latency and less errors; the number of error in the mice of the high- and intermediate-dosage groups using the inventive drug decreases significantly (P<0.05). The results are shown in Table 2.

TABLE 2

Influence on model of mice with ethanol induced memory retrieval impairment ($\bar{X} \pm SD$)

| Group | Dosage (mg/kg) | N | Latency (s) | Number of Mistakes |
|---|---|---|---|---|
| Control | | 10 | 234.3 ± 130.3 | 0.4 ± 0.9 |
| Model | | 10 | 204.9 ± 102.4 | 2.1 ± 2.0# |
| Huperzine A | 0.08 | 10 | 214.1 ± 127.8 | 1.0 ± 1.3 |
| Tanakan | 30 | 10 | 255.8 ± 69.5* | 0.4 ± 0.5* |
| Drug of This Invention | 11.5 | 10 | 221.5 ± 92.6 | 1.3 ± 1.1 |
| Drug of This Invention | 23 | 10 | 212.2 ± 128.2 | 0.7 ± 0.7* |
| Drug of This Invention | 46 | 10 | 253.7 ± 65.2 | 0.6 ± 0.7* |

Note:
compared with control group: #P < 0.05;
compared with model group: *P < 0.05.

1.3 Morris Water Maze Experiment

The experiment is performed as per the method described in Morris R G M, Garrud P, Rawlins J N P et al. *Place navigation impaired in rats with hippocampus lesions. Nature;* 297: 681~3.

1.3.1 Influence on Space Learning and Memory of Model of Rats Impaired by β-Amyloid Precursor Protein (Aβ) Toxicity.

Four weeks after CA1 region of bilateral hippocampus is injected with Aβ 1-40, the length of swimming time and route in the Morris water maze for the rats in the model group is longer, with the significant difference compared with the sham operation group (P<0.05). The search strategy is mostly marginal or random. Four weeks after CA1 region of bilateral hippocampus is injected with Aβ 1-40, the length of swimming time and route in the Morris water maze for the rats in the high and intermediate-dosage groups of the invention is much shorter than the model group (P<0.05), and the search strategy is mostly the taxis strategy. The results refer to Table 3.

TABLE 3

Influence on Space Learning and Memory of Model of Rats Impaired by β-amyloid precursor protein (Aβ) toxicity ($\bar{X} \pm SD$)

| Group | Dosage (mg/kg) | n | Length of time | Length of route |
|---|---|---|---|---|
| Sham operation | | 11 | 9.3 ± 5.1 | 268.9 ± 186.9 |
| Model | | 11 | 23.0 ± 9.1# | 696.3 ± 227.3## |
| Huperzine A | 0.08 | 11 | 16.3 ± 10.6 | 436.7 ± 284.4* |
| Drug of this invention | 11.5 | 11 | 11.6 ± 10.0* | 335.7 ± 413.6* |
| Drug of this invention | 23 | 11 | 11.3 ± 5.6* | 301.1 ± 179.1* |
| Drug of this invention | 46 | 11 | 10.1 ± 7.0* | 280.5 ± 250.6* |

Note:
Compared with sham operation group #P < 0.05, ##P < 0.01;
compared with model group *P < 0.05.

1.3.2 Influence on Space learning and Memory of VD Rats Undergoing Bilateral Common Carotid Artery Permanent Ligation (2VO)

One month after the bilateral common carotid artery of the rats is ligated, there is no significant difference compared with the sham operation group although there are the trend of learning and memory disorder. Two and three months after the ligation, the time of passing through the maze for the rats in the model group is significantly longer than the sham operation group (P<0.01), indicating that the learning and memory ability of the rats will decreases significantly with the lapse of the time of ischemia. One or two months after the drug is administered, the learning and memory ability of the rats in the three dosage groups of the inventive drug all significantly increases and the time of passing through the maze is significantly shortened compared with the model group (P<0.05~0.01); There are same effects in the Wei Nao Kang and Huperzine A groups (P<0.05~0.01); Two months after the drug is administered, the learning and memory ability of rats in the Tanakan group increases significantly (P<0.05); Compared with Nao Wei Kang, one or two months after the drugs of this invention are administered, the learning and memory ability of the rats in the large- and intermediate-dosage groups all increase significantly and the time of passing through the maze is significantly shortened compared with the model group (P<0.05~0.01). The results are shown in Table 4.

TABLE 4

Influence of drug of this invention on time of passing through maze for 2VO rats ($\bar{x} \pm s$)

| | | | Time (s) | | |
|---|---|---|---|---|---|
| Group | Dosage (mg/kg) | N | 1 month after ligation | 2 months after ligation | 3 months after ligation |
| Sham operation | | 10 | 36.8 ± 23.1 | 10.1 ± 5.3 | 8.2 ± 4.6 |
| Model | | 10 | 60.3 ± 26.1 | 55.2 ± 26.1## | 45.1 ± 23.2## |
| Huperzine A | 0.06 | 10 | 61.3 ± 25.2 | 29.1 ± 18.5* | 10.8 ± 5.6** |
| Tanakan | 20 | 10 | 59.7 ± 21.8 | 50.2 ± 29.1 | 22.2 ± 10.2* |
| Wei Nao Kang | 15 | 10 | 60.9 ± 27.5 | 34.3 ± 16.9* | 23.4 ± 12.6 |
| Drug of this invention | 11.5 | 10 | 61.2 ± 23.5 | 26.6 ± 10.2** | 15.6 ± 7.9** |
| Drug of this invention | 23 | 10 | 60.5 ± 26.7 | 19.5 ± 12.6Δ | 13.2 ± 6.6Δ |

TABLE 4-continued

Influence of drug of this invention on time of passing through maze for 2VO rats ($\bar{x} \pm s$)

| Group | Dosage (mg/kg) | N | 1 month after ligation | 2 months after ligation | 3 months after ligation |
|---|---|---|---|---|---|
| Drug of this invention | 46 | 10 | 60.8 ± 24.0 | 17.1 ± 11.4**△ | 7.6 ± 5.5**△△ |

Note:
compared with sham operation group: ##P < 0.01;
Compared with model group: *P < 0.05, **P < 0.01;
Compared with Nao Wei Kang: △P < 0.05, △△P < 0.01.

1.4 Discussion and Brief Summary (1) The pharmacodynamic experiments of scopolamine, chlorpromazine, reserpine or sodium nitrite induced injury are also performed in this invention. After the said chemical injury, the mouse step down experiment is performed with the escape latency and number of error in 5 minutes as the indices. 15 days after the intragastric administration of the drugs of this invention, the two indices are improved to different extent, indicating that the drug of this invention may improve the acquired and consolidated memory impairment of model mice.

(2) Based on the ethanol injury, the mouse step through experiment is performed with the escape latency and number of error in 5 minutes as the indices. 15 days after the intragastric administration of the drugs of this invention, the two indices are improved to different extent, indicating that the drug of this invention can improve the memory retrieval impairment of model mice.

(3) In this research, the D-galactose induced the brain aging rats, the Aβtoxicity impaired rats, the natural aging induced cognition impairment rats and APP transgenic mice serve as the AD model and 2VO rats as the VD model. The swimming length of time and route in 3 minutes serve as the main indices while search strategy and the like serves as the auxiliary indices. The influence of the drugs on the swimming scores of mice is observed. The results show that the swimming scores of rats or mice are improved to different extents after the intragastric administration of the drugs of this invention, indicating that the drugs of this invention can improve the space learning and memory ability of AD and VD model animals. Furthermore, compared with Wei Nao Kang, the drugs of this invention can significantly improve the indices of Morris water maze experiment for the 2VO rats, indicating that the therapeutic effect of the drug of this invention with the addition of *glycine max* l. merrill is better.

2 Detection of Neurotransmitter

The experiment is performed as per the method disclosed in Liu J X, Cong W H, Xu L, Wang J N., *Effect of combination of extracts of radix ginseng and ginkgo biloba on acetylcholine in amyloid beta-peptide-treated rats determined by an improved HPLC. Acta Pharmacol Sin.* 2004; 25: 1118~23.

2.1 Acetylcholine (Ach)

2.1.1 Influence on Content of Ach in Whole Brain of Rat Models with Aβtoxicity Injury Four weeks after CA1 region of bilateral hippocampus is injected with $A\beta_{1-40}$, the content of ACh in the whole brain of the rats in the model group decreases significantly compared with the sham operation group (P<0.01). Four weeks after the drug is administered, the content of Ach in the hole brain of the rats in all groups of the inventive drug increases significantly compared with the rats in the model group (P<0.05~0.01); There is the trend of increase in the level of Ach in the whole brain of rats in the positive Huperzine A group, but without significant difference. The results are shown in Table 5.

TABLE 5

Influence on content of Ach in whole brain of rats with Aβtoxicity injury ($\bar{X} \pm SD$)

| Group | Dosage (mg/kg) | n | Content of ACh (µg/l) |
|---|---|---|---|
| Sham operation | | 6 | 242.8 ± 39.7 |
| Model | | 6 | 155.7 ± 15.5## |
| Huperzine A | 0.08 | 6 | 180.0 ± 23.5 |
| Drug of this invention | 11.5 | 6 | 211.2 ± 39.3* |
| Drug of this invention | 23 | 6 | 227.8 ± 54.1* |
| Drug of this invention | 46 | 6 | 235.4 ± 25.4** |

Note:
Compared with sham operation ##P < 0.01;
Compared with model group *P < 0.05, **P < 0.01.

2.1.2 Influence on Ach in Whole Brain of Bilateral Common Carotid Artery Permanent Ligation Induced VD Rats The content of Ach in the brain of the rats in the model group decreases significantly 3 months after 2VO compared with the sham operation group (P<0.01); Two months after the drug is administered, the content of ACh in the rats of all groups of the inventive drug increases significantly (P<0.05~0.01); Wei Nao Kang, Huperzine A and Tanakan have same effects (P<0.05~0.01); Compared with Tanakan group, the content of ACH in the rats of the large- and intermediate groups of the inventive drug increases significantly (P<0.05~0.01).

The results are shown in Table 6.

TABLE 6

Influence of the drug of this invention on content of ACh in brain of 2VO rats ($\bar{x} \pm s$)

| Group | Dosage (mg/kg) | n | Content of ACh (µg/l) |
|---|---|---|---|
| Sham operation | | 10 | 284.4 ± 51.2 |
| Model | | 10 | 146.4 ± 13.2## |
| Huperzine A | 0.06 | 10 | 221.4 ± 41.9** |
| Tanakan | 20 | 10 | 182.4 ± 40.3* |
| Wei Nao Kang | 15 | 10 | 173.2 ± 23.6** |
| Drug of this invention | 11.5 | 10 | 183.3 ± 22.7** |
| Drug of this invention | 23 | 10 | 201.2 ± 31.2**△ |
| Drug of this invention | 46 | 10 | 218.1 ± 34.9**△△ |

Note:
Compared with sham operation group: ##P < 0.01;
Compared with model group: *P < 0.05, **P < 0.01;
Compared with Wei Nao Kang: △P < 0.05, △△P < 0.01.

2.1.3 Discussion and Brief Summary

After the intragastric administration of the drug of this invention, the content of ACh in the whole brain or hippocampus of the animal increases significantly, indicating that the drug of this invention can regulate the release and degradation of ACh in the said AD and VD animal model, increase ACh of the central nervous system and improve the its central cholinergic system. Moreover, compared with Nao Wei Kang, the content of ACh of the central system in 2VO rats with the drug of this invention increases significantly, indicating that the effect of the inventive drug with the addition of *glycine max* l. merrill is better.

2.2 Monoamine Neurotransmitters and its Metabolites 2.2.1 Influence on Content of Monoamine Neurotransmitters and its Metabolites in Whole Brain of Rat Models with Aβ Toxicity Injury Compared with the sham operation group, the content of 5-hydroxytryptamine (5-HT) in whole brain of the rats of the model group decreases significantly (P<0.05), and there is the trend of decrease for dopamine (DA) and norepinephrine (NE). Compared with the model group, there are no significant changes in DA and 5-HT of the whole brain of all inventive drug administering groups (P>0.05), and there is the trend of decrease for the level of homovanillic acid (HVA) and 5-hydroxyindoleacetic acid (5-HIAA), especially with the significant decrease of HVA for the low-dosage group of the inventive drug (P<0.05). The results are shown in Table 7.

5-HT. It is also found that the mechanism of the drug of this invention increasing DA and 5-HT level may be different from Huperzine A and Tabakan. Huperzine A may inhibit the metabolism of DA in the neurons and degradation of 5-HT while the Tanakan may inhibit the metabolism of DA in the neurons and the intake of 5-HT.

(3) The same pharmacodynamic experiment is also performed for the APP transgenic mice in this invention. Contrary to the change of the monoamine neurotransmitters in the brain of the above-said two AD models, the 5-HT and 5-HIAA in the whole brain of the APP transgenic mice increase significantly, and there is the trend of increase for NE and AD, indicating that the abnormal expression of the APP gene may affect the metabolism of the monoamine neurotransmitters in the central system in a mode different from other animal models, which is consistent with the reports in the literature. 5-HT and 5-HIAA in the positive Huperzine A group and the large-dosage group of the inventive drug

TABLE 7

Influence on content of monoamine neurotransmitters and its metabolites in whole brain of rat models with Aβ toxicity injury ($\overline{X} \pm SD$) Unit: µg/l

| Group | Dosage (mg/kg) | n | NE | DOPAC | DA | 5-HIAA | HVA | 5-HT |
|---|---|---|---|---|---|---|---|---|
| Sham operation | | 9 | 105.7 ± 16.5 | 17.2 ± 3.6 | 160.4 ± 36.5 | 39.7 ± 11.4 | 16.3 ± 3.3 | 59.3 ± 9.0 |
| Model | | 6 | 88.6 ± 19.5 | 13.7 ± 2.0 | 139.4 ± 14.2 | 35.6 ± 13.2 | 13.5 ± 4.2 | 42.6 ± 7.6# |
| Huperzine A | 0.08 | 6 | 75.9 ± 11.3 | 13.4 ± 1.3 | 136.2 ± 8.5 | 27.3 ± 3.1 | 15.4 ± 9.4 | 41.7 ± 5.9 |
| Drug of this invention | 11.5 | 6 | 85.6 ± 5.8 | 12.6 ± 2.0 | 137.3 ± 12.9 | 29.3 ± 6.2 | 9.4 ± 1.5* | 39.9 ± 8.4 |
| Drug of this invention | 23 | 6 | 82.2 ± 12.5 | 14.1 ± 2.4 | 135.7 ± 15.6 | 27.4 ± 3.6 | 13.1 ± 4.6 | 42.7 ± 8.8 |
| Drug of this invention | 46 | 6 | 84.7 ± 8.4 | 13.8 ± 1.9 | 137.3 ± 14.4 | 26.1 ± 2.0 | 12.4 ± 2.5 | 37.5 ± 10.8 |

Note:
compared with sham operation group #P < 0.05;
compared with model group *P < 0.05.

2.2.2 Discussion and Brief Summary (1) The low level of metabolism of monoamine neurotransmitters in the brains of the rats with Aβ toxicity injury is similar to the pathological changes of the aging and AD patients, indicating that the memory disorder caused by Aβ toxicity injury may be related to the change of the metabolism of the monoamine neurotransmitter DA and 5-HT. The drug of this invention may slow the degradation of DA and 5-HT and enhance the level of DA and 5-HT in the central system relatively to improve the activity of the monoaminergic system in the brain.

(2) The same pharmacodynamic experiment is also performed for the model of natural aging cognition impairment in this invention. It is found that DA, HVA, 5-HT and 5-HIAA in the hippocampus of the model rats all decrease significantly, and there is the trend of decrease for NE and dihydroxyphenylacetic acid (DOPAC), indicating the level of the activity of the metabolism of the monoamine neurotransmitters is low, which is consistent with the activity of NE, DA and 5-HT of the central system of the AD patients and the old people. 12 weeks after the drug of this invention is administered, there is the trend of increase for DA, DOPAC, 5-HT and 5-HIAA and the levels of DA and 5-HT in the hippocampus of the high-dosage group of this inventive drug increase significantly, indicating that it may improve the activities of DA and 5-HT system, perhaps by inhibiting the intake of the DA and decrease to different degrees, indicating that the both can regulate the activity of this system by regulating the abnormal metabolism of 5-HT of the central system.

The result shows that the drug of this invention can regulate the level of NE, DA and 5-HT of the central system and the activity of NE, DA and 5-HT system. In view of that the interaction (dependence and reinforcement) between cholinergic and monoaminergic systems participates in the process of cognition, the effect of improving learning memory of the drug of this invention may be related to its intervention for the intake and degradation of the monoamine neurotransmitter.

3 Detection of Other Biochemical Indices

The detection is performed as per the instruction of the reagent kits.

3.1 Acetylcholinesterase (AChE)

3.1.1 Influence on Activity of AChE of Whole Brain of Rat Models with Natural Aging Cognition Impairment Compared with the young control group, the activity of AChE of whole brain of rats in the old control group decreases significantly (P<0.05). 12 weeks after the drug is administered, compared the rats in the old control group, the activity of AChE of the whole brain of rats in the positive Huperzine A group, the Tanakan group and the groups of the inventive drug increases significantly (P<0.05~0.01). The results refer to Table 8.

TABLE 8

Influence on activity of AChE of whole brain of rat models with natural aging ($\overline{X} \pm SD$)

| Group | Dosage (mg/kg) | n | Activity of AChE (U/mgProt) |
|---|---|---|---|
| Young control | | 7 | 1.31 ± 0.26 |
| Old control | | 15 | 0.88 ± 0.28# |
| Huperzine A | 0.08 | 7 | 1.18 ± 0.19* |
| Tanakan | 30 | 7 | 1.19 ± 0.22* |
| Drug of this invention | 11.5 | 7 | 1.49 ± 0.47* |
| Drug of this invention | 23 | 7 | 1.51 ± 0.16** |
| Drug of this invention | 46 | 7 | 1.31 ± 0.17** |

Note:
compared with young control group #P < 0.05;
compared with old control group *P < 0.05, **P < 0.01.

3.2 Malondialdehyde (MDA)

3.2.1 Influence on Content of MDA of Whole Brain of Rat Models with Natural Aging Cognition Impairment Compared with the young control group, the content of MDA of whole brain in the rats of the old control group increases significantly (P<0.05). 12 weeks after the drug is administered, the content of MDA of whole brain of the rats in all the groups of the inventive drug decreases significantly (P<0.05). There is the trend of decrease in the content of brain MDA of the rats in the positive Huperzine A group and the Tanakan group, but without significant differences (P>0.05). The results are shown in Table 9.

TABLE 9

Influence on content of MDA of whole brain of rat models with natural aging cognition impairment ($\overline{X} \pm SD$)

| Group | Dosage (mg/kg) | n | Content of MDA (nmol/mgProt) |
|---|---|---|---|
| Young control | | 7 | 2.97 ± 0.20 |
| Old control | | 7 | 4.46 ± 1.41# |
| Huperzine A | 0.08 | 7 | 3.50 ± 0.43 |
| Tanakan | 30 | 7 | 4.35 ± 0.66 |
| Drug of this invention | 11.5 | 7 | 3.16 ± 0.61* |
| Drug of this invention | 23 | 7 | 3.08 ± 0.73* |
| Drug of this invention | 46 | 7 | 3.17 ± 0.25* |

Note:
compared with young control group #P < 0.05;
compared with old control group *P < 0.05.

3.3 Superoxide Dismutase (SOD)

3.3.1 Influence on Activity of Sod of Whole Brain of Rat Models with Natural Aging Cognition Impairment Compared with the young control group, the activity of SOD of whole brain in the old control group decreases significantly (P<0.05). 12 weeks after the drug is administered, compared with the rats in the old control group, the activity of SOD of the whole brain of the rats in the positive Huperzine A group, the Tanakan group and all the inventive drug groups increases significantly (P<0.05). The results are shown in Table 10.

TABLE 10

Influence on activity of SOD of whole brain of rats with natural aging cognition impairment ($\overline{X} \pm SD$)

| Group | Dosage (mg/kg) | n | Activity of SOD (NU/mgProt) |
|---|---|---|---|
| Young control | | 7 | 44.34 ± 7.66 |
| Old control | | 7 | 32.22 ± 12.77# |
| Huperzine A | 0.08 | 7 | 43.68 ± 2.55* |
| Tanakan | 30 | 7 | 40.18 ± 4.74* |
| Drug of this invention | 11.5 | 7 | 46.84 ± 3.47* |
| Drug of this invention | 23 | 7 | 47.94 ± 6.07* |
| Drug of this invention | 46 | 7 | 45.16 ± 5.83* |

Note:
compared with young control group #P < 0.05;
compared with old control group *P < 0.05.

3.4 Influence on Activity of Whole Brain $Na^+$-$K^+$-ATP Enzyme of Rats with Aβ Toxicity Impairment Compared with the sham operation group, four weeks after the CA1 region of bilateral hippocampus is injected with $A\beta_{1-40}$, the activity of whole brain $Na^+$-$K^+$-ATP enzyme of rats decreases significantly (P<0.05); Four weeks after the drug is administered, compared with the rats of the model group, the activity of whole brain $Na^+$-$K^+$-ATP enzyme of the rats in the Huperzine A group, the Tanakan group and all the inventive drug groups increases significantly (P<0.05~0.01). The results refer to Table 11.

TABLE 11

Influence on activity of whole brain $Na^+$—$K^+$-ATP enzyme of rats with Aβ toxicity impairment ($\overline{X} \pm SD$)

| Group | Dosage (mg/kg) | n | Activity of $Na^+$—$K^+$-ATP (μmoLPi/mgProt/h) |
|---|---|---|---|
| Sham operation | | 7 | 0.205 ± 0.037 |
| Model | | 7 | 0.161 ± 0.013# |
| Huperzine A | 0.08 | 7 | 0.207 ± 0.025* |
| Drug of this invention | 11.5 | 7 | 0.218 ± 0.018** |
| Drug of this invention | 23 | 7 | 0.195 ± 0.012** |
| Drug of this invention | 46 | 7 | 0.193 ± 0.032* |

Note:
compared with the sham operation group #P < 0.05;
compared with the model group *P < 0.05, **P < 0.01.

3.5 Discussion and Brief Summary 3.5.1 Influence on Activity of AChE (1) The activity of whole brain AChE of rats with natural aging cognition impairment decreases significantly, which is consistent with the changes of the aging and AD. The drug of this invention can remarkably increase said lowered activity of AChE, regulate the abnormal metabolism state and improve the function of the central cholinergic nervous system as well as the learning memory disorder in the aging or AD.

(2) The same pharmacodynamic experiments are also performed for the rats with D-galactose induced brain aging and the APP transgenic mice. The activity of whole brain AChE of the two model animals all increase significantly and the too high activity accelerate the degradation of ACh. The drug of this invention can inhibit the activity of whole brain AChE of the two mode animals significantly and may slow down the degradation metabolism of ACh to increase the level of ACh and improve the learning and memory.

3.5.2 Influence on Content of MDA and Activity of SOD

After the drug is administered for the rats with the natural aging cognition impairment, the activity of SOD of whole brain increases while the level of MDA decreases, indicating that the drug of this invention may improve the function of anti-oxidation and removal of free radicals of the old animals, and help anti-aging and improve memory ability.

3.5.3 Influence on Activity of Whole Brain $Na^+$-$K^+$-ATP Enzyme of Rats with Aβ Toxicity Impairment After the drug is administered, the activity of whole brain $Na^+$-$K^+$-ATP enzyme of rats with Aβ toxicity impairment increases significantly, indicating that the drug of this invention may protect the activity of ATP enzyme and regulate the cell transportation to improve the function of plasma membrane of nerve cells and the cellular function.

4. Detection of Expression Level of APP Gene 4.1 Influence on Expression Level of APP Gene of Cortex and Hippocampus of Rats with Natural Aging Cognition Impairment Compared with the young control group, the level of expression of APP gene of cortex and hippocampus of rats in the old control group increases significantly ($P<0.05$). 12 weeks after the drug is administered, compared with the old control group, the level of expression of APP gene in the positive Tanakan group and the all dosage groups of the inventive drug decreases significantly ($P<0.05$). The results are shown in Table 12.

TABLE 12

Influence on expression level of APP gene of cortex and hippocampus of rats with natural aging cognition impairment ($\bar{X} \pm SD$)

| Group | Dosage (mg/kg) | n | APP/β-actin (%) |
|---|---|---|---|
| Young control | | 3 | 87.8 ± 10.8 |
| Old control | | 3 | 143.4 ± 16.9# |
| Tanakan | 30 | 3 | 104.4 ± 6.6* |
| Drug of this invention | 11.5 | 3 | 101.4 ± 20.9* |
| Drug of this invention | 23 | 3 | 108.4 ± 15.0* |
| Drug of this invention | 46 | 3 | 97.2 ± 22.5* |

Note:
compared with young control #$P < 0.05$;
compared with old control *$P < 0.05$.

4.2 Discussion and Brief Summary

The results show that the drug of this invention can significantly regulate the over-expression of APP gene of cortex and hippocampus of rats with natural aging cognition impairment, indicating that the improvement of the learning memory impairment by the drug may be due to its inhibition to the abnormal expression of this gene in the cortex and the hippocampus, decreasing the formation and abnormal deposition of Aβ and the formation of SP, intervening the pathological impairment probably induced by Aβ from the upstream of the pathological changes and affecting the factors related to the central learning memory function.

5 Histological and Cellular Morphological Experiment 5.1 HE Staining

The experiment is performed as per Section 2, Chapter 7 of *Pathological Tissue Sectioning and Staining Technology* (Gong Zhi-jin et al.).

5.1.1 Influence on Histomorphology of Rat Models with D-Galactose Induced Brain Aging The pyramidal cells of hippocampus of rats in the blank group are tight in alignment, obvious with the upper and lower cell lines and rich in number of cells; the nuclear membrane are clear with distinct nucleolus. The pyramidal cells of hippocampus of rats in the model group is loosening in the alignment, oblique in the cellular structure, swelling in the cell body and irregular in the upper and lower cell lines; Some cells have nucleus pyknosis and deep staining. Compared with the model group, the pyramidal cells of hippocampus of rats in the positive Huperzine A group and all the inventive drug groups are in order of alignment with clearer contour of cells; and there are less nucleolus pyknosis and the deep staining. Especially, the effects in the Huperzine A group and the high- and intermediate-dosage groups of the invention are more evident.

5.1.2 Influence on Histomorphology of Rat Models with Natural Aging Cognition Impairment The pyramidal cells of hippocampus of rats in the young control group are concentrated in alignment, evident in the upper and lower cell lines and well-shaped in contour, and the nucleus membrane is clear with obvious nucleolus. The pyramidal cells of hippocampus of rats in the old control group are loosening in alignment and some cells have incomplete structure; A few nucleus appear pyknosis and deep staining with triangular contour; compared with the old control group, the pyramidal cells of hippocampus of rats in the Tanakan group and all the inventive drug groups have clearer alignment and better cellular morphology, and there are less nucleolus pyknosis and deep staining. Especially, the effect in the Tanakan group and all the high- and intermediate-dosage groups of the inventive drug is more evident.

5.2 Influence on Ultrastructure of Hippocampus Nerve Cells

The method used is as per Page 1-4 of *Modern Medical Experimental Method* (Wang Qian)

5.2.1 Influence on Ultrastructure of Hippocampus Nerve Cells of Rat Models with Aβ Toxicity Impairment The ultrastructure of hippocampus nerve cells of rats in the sham operation group is normal with big round or oval nucleus, uniform euchromatin, evident nucleolus and intact nucleus membrane; the structure of the mitochondria and rough endoplasmic reticulum in the cytoplasm is clear; and there are rich ribosome and synapses. There are margination and pyknosis of chromosome of nucleus of hippocampus nerve cells in rats of the model group; the volume of cell is lessened and the cytoplasm is concentrated; the mitochondria are mildly swelling in a few cells; the cell organelle such as the rough endoplasmic reticulum and ribosome are generally normal; and the presynaptic and postsynaptic membranes are not clear. The synaptic space disappears. There are significantly less synaptic vesicles than the sham operation group. Compared with the model group, the hippocampus nerve cells in the Huperzine A group and all the groups of the inventive drug have better morphology and structure, clearer cell membrane and pre- and post-synaptic membranes; most cells have uniform chromosome of nucleus; and the mitochondrial cristae are clearer.

5.2.2 Influence on Ultrastructure of Hippocampus Nerve Cells of Rat Models with Natural Aging Cognition Impairment The hippocampus nerve cells in the young control group keep the characteristics of normal morphology with big round or oval nucleus and uniform chromatin and evident nucleolus; the structure of the mitochondria and rough endoplasmic reticulum in the cytoplasm is clear; and there are rich ribosome and synapses. There are obvious fragmentation and lysis of membrane, vacuole and myeloid structure in some hippocampus nerve cells in the old control group; the nucleus is irregular in form, the chromatin is agglomerated and the nucleus peripheral space is significantly thickened; the mitochondria is swelling and vacuolated; the endoplasmic reticulum is extended; and a lot of lipofuscin and oil drops are found. Contrary to the model group, in the Huperzine A group and all the groups of the inventive drug, the hippocampus nerve cells have better morphology and structure and clearer cell membrane; some cells have uniform chromosome of nucleus; the lamellar mitochondrial cristae are clearer; the number of ribosome increases; and the number of synapse increases. Especially, the effect in the Tanakan group and all the high- and intermediate-dosage groups of the inventive drug is more evident.

5.2.3 Influence on Ultrastructure of Hippocampus Nerve Cell Models of APP Transgenic Mice The ultrastructure of the hippocampus nerve cells of the non-transgenic mice littermates is normal with big round or oval nucleus, uniform chromatin and evident nucleolus; the structure of the mitochondria and rough endoplasmic reticulum in the cytoplasm is clear; there are rich ribosomes; and there are a lot of synapses. The nucleus in the blank mice group have pyknosis, margination and irregular alignment; the mitochondria are few, the cristae are not in order and the critae space is big; the rough endoplasmic reticulum is not in order and even fragmented; the lysosome is increased in number with the irregular shape; the vacuole, the myeloid structure and irregular lipofuscin can be found in the cytoplasm. Compared with the blank group, the cells in the high-dosage group of this inventive drug have better morphology and structure and some cells have clearer structure; and some nucleus have uniform chromatin.

5.3 Brief Summary

The intact morphology and structure of hippocampus nerve cells is the premise that they can function normally. The pathological factors such as the ischemic cerebrovascular disease, the aging or the senile dementia can induce the impairment of the morphology and structure of the nerve cells, which will result in the abnormality of the functions inevitably. For example, the impairment of the nucleus and the rough endoplasmic reticulum can induce the decrease of the function of the synthesis of protein; the injury of the mitochondria can induce the disorder of the energy metabolism; the accumulation of lots of lipofuscin will disturb the arrangement in the space; the loss of the synapses will means the loss of the target tissue for the nerve cells; and all the changes eventually result in the aging and death. The rats with the D-galactose induced brain aging and the rats with the natural aging cognition impairment serve as the models for HE staining, and the rats with the Aβtoxicity injury, the rats with the natural aging cognition impairment and the APP transgenic mice serve as the model for transmission electron microscopy to investigate the influence of the drug of this invention on the hippocampus nerve cells of the model animals. The results show that for different model animals administered with the drug of this invention, the morphology and the structure of the hippocampus nerve cells and synapses can be improved to different extents, the number of synapse increases, the apoptosis and loss of the nerve cells can be retarded or lessened, indicating that the drug of this invention may protect the nerve cells.

Toxicological Test

The rats with fasting for 16 hours undergo the intragastric administration with the dosage of the maximal concentration (57.5 mg/ml) and the maximal volume (20 ml/kg body weight), twice daily. The daily maximal dosage is 2300 mg/kg body weight and equals to the 670-fold clinical dosage for human being (240 mg/day). After consecutive 14 days' observation, no death is observed. The rats are administered with the drug of the 70-, 35- and 17.5-fold clinical dosage planned to be prescribed for human being for 6 months. The general condition, the body weight, the food intake, the blood routine, the blood coagulation, blood biochemistry, the ECG, and the indexes and macro and microscopic inspection of main viscera are investigated 3, 6 months after the drug is administered and 4 weeks after the drug administering is stopped respectively. No significant pathological changes are found. The toxicological research shows that the drug is safe with low toxicity.

In summary, the composition of this invention is better than the commonly used drugs in treatment of the ischemic cerebrovascular disease and the senile dementia and has significant effect. The long-term study also shows that the traditional Chinese medicine composition of this invention is stable and reliable.

BEST MODE FOR CARRYING OUT THE INVENTION

The aim and technical solution of invention are illustrated in details with the following examples.

Example 1

The Preparation of the Chinese Medicine Composition (Extracts) of this Invention Formula:

| | | | |
|---|---|---|---|
| Extract of radix *ginseng* | 27.5 g | Extract of folium *ginkgo* | 27.5 g |
| Extract of stigma *croci* | 5.5 g | Extract of *glycine max* l. merrill | 2.75 g. |

Method of Preparation:

60% ethanol of 8-fold quantity of radix ginseng crude drug is added into the radix ginseng and the reflux extraction is performed twice. The liquid extracts are combined and concentrated till the relative density is around 1.05 (50° C.). The liquid concentrate is added with distilled water of 2-fold volume and filtered. The filtrate is chromatographed on the AB-8 Type macroporous adsorptive resin. The resin with drugs is eluted by distilled water, followed by 10% ethanol. The water and 10% ethanol eluent is discarded and the resin is eluted with the 70% ethanol till the volume is about 2.5-fold of the volume of the column. The 70% ethanol eluent is collected and the extract of radix ginseng containing the ginsenosides can be obtained.

70% ethanol of 8-fold quantity of dry folium ginkgo are added into the folium ginkgo, immersed at 60° C. and extraction is performed twice, at least one hour once. The liquid extracts are combined and concentrated by decompression till the relative density is around 1.05 (50° C.). The liquid concentrate is added with water, cooled, precipitated and filtered. The filtrate is chromatographed on the ADS-17 Type macroporous adsorptive resin. The resin with drugs is eluted by water, followed by 60% ethanol. The water eluent is discarded while the 60% ethanol eluent is collected and concentrated till there is no smell of alcohol. Then water of 2-fold quantity of the crude drugs is added and heated to boiling. Precipitation at room temperature goes for 24 hours. After filtering, the filtrate is chromatographed on the DM-130 Type macroporous adsorptive resin. The resin with drugs is eluted by water, followed by 15% ethanol and 60% ethanol. The water and 15% ethanol eluents are discarded while the 60% ethanol eluent is collected. Concentration and drying continue until the product of the extract of the folium ginkgo can be obtained. The ratio of the content of the ginkgo flavonoids to the ginkgolides in the product is 24:15.

60% ethanol of 20-fold quantity of stigma croci crude drug are added into the stigma croci materials, immersed at 70-80° C. and extraction is performed twice. The liquid extracts are combined and concentrated till there is no smell of alcohol. The liquid concentrate is added and diluted with water of more than 1-fold quantity of crude drug. The diluted liquid is chromatographed on the AB-8 Type macroporous adsorptive resin. The resin with drugs is eluted by water, followed by 20%, 30% and finally 70% ethanol is used for elution. The water eluent and 30% ethanol eluent are discarded while the 70% ethanol eluent is collected and the extract of stigma croci including stigma croci glycosides can be obtained.

The *glycine max* l. merrill is extracted with 95% ethanol and filtered. The residue is extracted with 70% ethanol and filtered. The ethanol extracts are combined and concentrated till there is no smell of alcohol. The water of 2-fold weight of materials is added, sufficiently stirred and filtered. The filtrate is chromatographed on the AB-8 type macroporous adsorptive resin. The resin with drugs is first eluted with water and the water eluent is discarded. Then 60% ethanol is used for elution. The eluent is collected and part A is obtained. The main components in part A is isoflavonoids. 90-95% ethanol is used for elution. The eluent is collected. The anhydrous ethanol is added for esterification. The water is added again for washing and the solution is stratified. The solution is decompressed to 0.1 MPa for degasification with a rotary evaporator after the lower layer (the acid water) is removed. The sodium hydroxide is added for alcoholysis. Then the water is added for washing. The alkaline water at the lower layer is removed. The organic liquid on the top layer is decompressed to 0.1 MPa for degasification and then undergoes the membrane distillation. The residue undergoes the molecular distillation (under 0.133 Pa, <0.5 mm between the evaporation plate and the condensation plate). The part B is obtained and its components are the mixed tocopherol. Parts B and A are mixed and used as the extract of the *glycine max* l. merrill in this invention. There are mainly the *glycine max* l. merrill isoflavonoids and the Vitamin E in the extract of *glycine max* l. merrill of this invention, with the ratio of weight 4:1.

The said dried extracts are crushed into 20 Mesh, added with 86.75 g of starch, put into the Capsule No. 3 and the capsule of this invention is produced.

The result shows that the capsule of the Chinese medicine composition accords with the following related regulation.

Qualification and Quantification: The identification and determination of the content of the ginkgolides are performed as per the section of the extract of folium ginkgo of Chinese Pharmacopoeia; The identification and determination of the content of the stigma croci glycosides I are performed as per the section of stigma croci Chinese Pharmacopoeia; The identification and the determination of the content of the radix ginseng are performed as per the section of radix ginseng of Chinese Pharfmacopoeia.

The method of determination of *glycine max* l. merrill isoflavonoid and genistein: the appropriate amount of the *glycine max* l. merrill extract is accurately weighted and added with 25 ml water. After mixing and suspending, 1 ml acetate buffer solution (pH4.5) and 15 μl β-glucosaccharase are added. The 37° C. water bath is used for hydrolysis. The solvent is recovered under reduced pressure till drying. The methanol is used for dissolution. The microporous filter membrane is used for filtering. The liquid chromatography is used for analysis (Zorbax-$C_{18}$ chromatography column. The mobile phase is methanol-water-acetic acid 45:55:1, flow velocity: 0.8 ml/min, wavelength of monitoring: 260 nm).

Determination of content of VE: the appropriate amount of this product is taken, accurately weighted and put into a mortar. Two drops of anhydrous ethanol are added into the mortar and the product is ground. 20 ml anhydrous ethanol is used for transferring the product quantitatively into the powder and liquid funnel by several times. 10 ml water is added and the n-hexane extraction is performed three times, 5 ml n-hexane once. The extraction liquids are combined. The solvent is recovered and dried under reduced pressure. The mobile phase of residue is transferred quantitatively into the 1 ml bottle. The mobile phase is added to the designated scale. The liquid in the bottle is shaken evenly and passes through the 0.45 μm microporous filter membrane as the test liquid. 10 μl each of the control liquid and the test liquid are taken and injected into the liquid chromatography for determination (97:3 v/v methanol-water serves as the mobile phase, the detection wavelength is 207 nm).

The composition in each capsule of the combination of drugs is as follows (1.5 g for each capsule):

(1) The total glycosides are not less than 13.75 mg on the basis of ginsenosides Re ($C_{48}H_{82}O_{18}$);

(2) On the basis of ginsenosides $Rg_1$ ($C_{42}H_{72}O_{14}$), Re ($C_{48}H_{82}O_{18}$) and ginsenosides $Rb_1$ ($C_{54}H_{92}O_{23}$), the total glycosides are not less than 1.375 mg, 0.825 mg and 0.825 mg respectively;

(3) The total flavonoids are no less than 11.00 mg, on the basis of rutin ($C_{27}H_{30}O_{16}$).

(4) The total flavonoid glycoside is not less than 6.60 mg, on the basis of quercetin, kaemferide and isorhamnetin respectively.

(5) The terpene lactone is not less than 2.75 mg based on the sum of ginkgolides A ($C_{20}H_{24}O_9$), ginkgolides B ($C_{20}H_{24}O_{10}$), ginkgolides C($C_{20}H_{24}O_{11}$) and bilobalide ($C_{15}H_8O_8$);

(6) The total stigma croci glycosides is not less than 2.75 mg on the basis of anhydrous stigma croci glycoside-I ($C_{44}H_{64}O_{24}$);

(7) The stigma croci glycoside-I ($C_{44}H_{64}O_{24}$) is not less than 1.375 mg (8) The total *glycine max* l. merrill isoflavonoids are not less than 1.35 mg on the basis of genistein ($C_{27}H_{30}O_{16}$);

(9) The genistein ($C_{27}H_{30}O_{16}$) is not less than 0.5 mg

(10) The vitamin E is not less than 0.5 mg on the basis of Vitamin E ($C_{31}H_{52}O_3$).

The clinical recommendation dosage of the capsule of the inventive composition is 150 mg, three times daily.

Example 2

The Formula for the Composition of this Invention is as Follows

| Radix ginseng | 40 parts by weight | Folium *ginkgo* | 45 parts by weight |
|---|---|---|---|
| Stigma *croci* | 1 part by weight | *Glycine max* l. merrill | 75 parts by weight |

Method of preparation of composition: the said medicinal materials are crushed into 20 Mesh, and the composition is achieved.

Preparation of granules: after the said drug powder is mixed, the dextrin and steviosin are added, mixed evenly, dried in vacuum at 70~75° C. Pulverized and granulated. The dark brown product granules of the composition of this invention are obtained.

The results show that the granules of the composition of this invention conform to the regulations under the section of granules (*Chinese Pharmacopoeia, 2005 edition volume Appendix IC*). The content of the components is detected as per Example 1, and ginsenosides Re is not less than 9.15 mg/g.

Example 3

Formula: extract of radix ginseng: 2 parts; extract of folium ginkgo: 10 parts; extract of stigma croci: 0.5 parts; extract of *glycine max* l. merrill: 1 part.

Method of preparation of tablets: after the extracts of the composition of this invention are mixed, the agglutinants such as dextrin are added, mixed sufficiently, dried in vacuum at 60-80° C. and pulverized. The fillers such as starch and lubricants such as magnesium stearate as well as the disintegrating agent such as sodium carboxymethyl starch are added and mixed evenly. The mixture is granulated and pressed into the tablets. The product tablets are obtained.

The result shows that the tablets of the composition of this invention conform to the related regulation under the section of the tablets. The quantification and quantification detection are performed as in Example 1. The product contains ginsenoside Re of no less than 9.15 mg/g.

Example 4

Formula: extract of radix ginseng: 10 parts; extract of folium ginkgo: 3 parts; extract of stigma croci: 4 parts; extract of *glycine max* l. merrill: 0.2 parts.

Method of preparation of composition: same as Example 1

Preparation of tablets: after the extracts of the composition of this invention are mixed, the agglutinants such as dextrin are added, mixed sufficiently, dried in vacuum at 60-80° C. and pulverized. The fillers such as starch and lubricants such as magnesium stearate as well as the disintegrating agent such as sodium carboxymethyl starch are added and mixed evenly. The mixture is granulated and pressed into the tablets. The product tablets are obtained.

The result shows that the tablets of the composition of this invention conform to the related regulation under the section of the tablets. The quantification and quantification detection are performed as Example 1. The product contains ginsenoside Re of no less than 9.15 mg/g.

Example 5

Formula: extract of radix ginseng: 10 parts; extract of folium ginkgo: 1 part; extract of stigma croci: 0.5 parts; extract of *glycine max* l. merrill: 80 parts.

Method of preparation: the said medicinal materials are crushed into 20 Mesh and the composition of this invention is obtained. The content of the components is determined as per Example 1, and the ginsenosides are not less than 9.15 mg/g.

The invention claimed is:

1. A composition comprising 1-10 parts by weight of radix ginseng or an extract thereof, 1-10 parts by weight of folium ginkgo or an extract thereof, 0.05-0.5 parts by weight of stigma croci or an extract thereof, and 5-10 parts by weight of *glycine max* l. merrill or an extract thereof.

2. The composition of claim 1, wherein the composition is as follows: 2-6 parts by weight of radix ginseng or an extract thereof, 3-6 parts by weight of folium ginkgo or an extract thereof, 0.06-0.2 parts by weight of stigma croci or an extract thereof, and 7-8 parts by weight of *glycine max* l. merrill or an extract thereof.

3. A composition comprising 1-10 parts by weight of the extract of radix ginseng, 1-10 parts by weight of the extract of folium ginkgo, 0.5-5 parts by weight of the extract of stigma croci and 0.1-1 parts by weight of the extract of *glycine max* l. merrill.

4. The composition of claim 3, wherein the said extract of folium ginkgo at least comprises ginkgo flavonoids and ginkgolides with a weight ratio of 24:25-10.

5. The composition of claim 4, wherein the said extract of folium ginkgo is obtained as follows:
60-80% ethanol of at least 2-fold quantity is added to the folium ginkgo and the immersion extraction is performed at least once at 50-70° C. to obtain liquid extracts;
the liquid extracts are combined and concentrated until the relative density of the resulting liquid concentrate is around 1.05;
water is added to the liquid concentrate and filtering the resulting mixture to obtain a filtrate;
the filtrate is chromatographed on the polar hydrogen bond polystyrene type macroporous adsorptive resin, the resin with drugs is eluted by water, followed by 60% ethanol, and the water eluent is discarded while the ethanol eluent is collected and concentrated till there is no smell of alcohol to get a concentrated eluent;
water is added to the concentrated eluent and filtering to get another filtrate, the filtrate is chromatographed on the weak polar polystyrene type macroporous adsorptive resin, the resin with drugs is eluted by water, followed by 15% ethanol and 60% ethanol respectively, and the water and 15% ethanol eluents are discarded while the 60% ethanol eluent is collected.

6. The composition of claim 3, wherein the said extract of the *glycine max* l. merrill comprises *glycine max* l. merrill isoflavonoid and Vitamin E in a weight ratio of 4:2-0.5.

7. The composition of claim 6, wherein the extract of *glycine max* l. merrill is obtained as follows:
material *glycine max* l. merrill is extracted with 85-95% ethanol and filtered, and the resulting residue is extracted further with 60-80% ethanol and filtered;
the resulting ethanol extracts are combined and concentrated until there is no smell of alcohol to get a concentrated extract, and the water of 1-fold weight of materials is added into the concentrated extract and filtered to get a filtrate;
the filtrate is chromatographed on the macroporous adsorptive resin, 50-65% ethanol is used for elution of the macroporous adsorptive resin, the resulting eluent is collected as part A;
90-95% ethanol is used further for elution of the macroporous adsorptive resin, and the 90-95% ethanol eluent is collected and evaporated to get a residue;
anhydrous ethanol is added into the residue for esterification, then water is added again and the resulting solution is stratified, and the solution is decompressed to 0.1 MPa for degasification after the lower layer of the solution is removed;
sodium hydroxide is added for alcoholysis, then water is added for washing, the washing liquid at the lower layer is removed, and the organic liquid on the top layer is decompressed to 0.1 MPa for degasification and then undergoes the membrane distillation;

the residue undergoes the molecular distillation to obtain part B;

Parts B and A are mixed.

8. A method of preparing the composition of claim 3, comprising: mixing the extract of radix ginseng, the extract of folium ginkgo, the extract of stigma croci and the extract of *glycine max* l. merrill;

wherein the said extract of radix ginseng is obtained as follows:

50-70% ethanol of at least 2-fold quantity of radix ginseng is added and the reflux extraction is performed at least once; liquid extracts are concentrated until the relative density of the resulting liquid concentrate is around 1.05; the liquid concentrate is added with water of at least one-fold volume and filtered; the filtrate is chromatographed on the low-polar polystyrene type macroporous adsorptive resin; the resin with drugs is eluted by water, followed by 10% ethanol; the water eluent and 10% ethanol eluent are discarded and the resin is eluted further with 60-75% ethanol, and the 60-75% ethanol eluent is collected and the extract of radix ginseng is obtained;

the said extract of folium ginkgo is obtained as follows:

60-80% ethanol of at least 2-fold quantity of dry folium ginkgo is added and at least one time of extraction is performed at 50-70° C.; the liquid extracts are concentrated by decompression till the relative density of the resulting liquid concentrate is around 1.05;

the liquid concentrate is added with water, cooled, precipitated and filtered; the filtrate is chromatographed on the polar hydrogen bond polystyrene type macroporous adsorptive resin; the resin with drugs is eluted by water, followed by 60% ethanol; the water eluent is discarded while the 60% ethanol eluent is collected and concentrated until there is no smell of alcohol; water is added and heated to boiling; precipitation is conducted at room temperature; after filtering, the filtrate is chromatographed on weak polar polystyrene type macroporous adsorptive resin; the resin with drugs is eluted by water, followed by 15% ethanol and 60% ethanol respectively; and the water and 15% ethanol eluents are discarded while the 60% ethanol eluent is collected;

the said extract of the stigma croci is obtained as follows:

60-80% ethanol of at least 5-fold quantity of stigma croci are added and at least one time of extraction is performed at 70-80° C.; the liquid extracts are concentrated until there is no smell of alcohol; the liquid concentrate is added and diluted with water of more than 1-fold of volume of crude drug; the diluted liquid is chromatographed on the weak polar polystyrene type macroporous adsorptive resin; the resin with drugs is eluted by water, followed by gradually increased concentration of less than 30% ethanol; finally 70% ethanol is used for elution of the resin with drugs; and the water eluent and less than 30% ethanol eluents are discarded while the 70% ethanol eluent is collected;

the said alcohol extract of *glycine max* l. merrill is obtained as follows:

material *glycine max* l. merrill is extracted with 85-95% ethanol and filtered; the residue is extracted with 60-80% ethanol and filtered; the ethanol extracts are combined and concentrated until there is no smell of alcohol; the water of 1-fold weight of the material is added into the resulting concentrate, then the mixture is filtered; the filtrate is chromatographed on the macroporous adsorptive resin; the resin with drugs is first eluted with water and the water eluent is discarded, then 50-65% ethanol is used for elution; the eluent is collected as Part A; 90-95% ethanol is used for further elution of the resin; the eluent is completely collected; anhydrous ethanol is added for esterification; the water is added again and the resulting solution is stratified; the solution is decompressed to 0.1 MPa for degasification after the lower layer of the solution is removed; sodium hydroxide is added for alcoholysis; water is added for washing; the water washing liquid at the lower layer of the resulting liquid is removed;

the organic liquid on the top layer is decompressed to 0.1 MPa for degasification and then undergoes the membrane distillation; the residue undergoes the molecular distillation to obtain Part B; and Parts B and A are mixed and used as the extract of *glycine max* l. merrill.

9. A drug for the treatment of ischemic cerebrovascular disease and senile dementia, the drug comprising the composition of claim 1 and a pharmaceutically acceptable auxiliary material.

10. The drug of claim 9, wherein the drug is formulated into a dosage form for oral medicament selected from honeyed pill, concentrated pill, watered pill, granule, capsule, tablet, powder, ointment, oral liquid or syrup.

11. A drug for the treatment of ischemic cerebrovascular disease and senile dementia, the drug comprising the composition of claim 3 and a pharmaceutically acceptable auxiliary material.

12. The drug of claim 11, wherein the drug is formulated into a dosage form for oral medicament selected from honeyed pill, concentrated pill, watered pill, granule, capsule, tablet, powder, ointment, oral liquid or syrup.

13. A method for the treatment of ischemic cerebrovascular disease or senile dementia in a subject, the method comprising administering to a subject in need thereof the composition of claim 1.

14. A method for the treatment of ischemic cerebrovascular disease or senile dementia in a subject, the method comprising administering to a subject in need thereof the composition of claim 3.

* * * * *